(12) United States Patent
Alitalo et al.

(10) Patent No.: US 10,731,117 B2
(45) Date of Patent: Aug. 4, 2020

(54) BIOREACTOR AND FERMENTATION PROCESS FOR PRODUCING HYDROGEN

(71) Applicant: Qvidja Kraft Ab, Lielahti TL (FI)

(72) Inventors: Anni Alitalo, Lielahti (FI); Erkki Aura, Lielahti (FI); Marko Niskanen, Lielahti (FI)

(73) Assignee: Q POWER OY, Lielahti TL (FI)

( * ) Notice: Subject to any disclaimer, the term of this patent is extended or adjusted under 35 U.S.C. 154(b) by 130 days.

(21) Appl. No.: 15/536,002

(22) PCT Filed: Dec. 14, 2015

(86) PCT No.: PCT/FI2015/050880
§ 371 (c)(1),
(2) Date: Jun. 14, 2017

(87) PCT Pub. No.: WO2016/097478
PCT Pub. Date: Jun. 23, 2016

(65) Prior Publication Data
US 2017/0342362 A1    Nov. 30, 2017

(30) Foreign Application Priority Data

Dec. 19, 2014  (FI) ..................................... 20146125

(51) Int. Cl.
| C12M 1/107 | (2006.01) |
| C12M 1/16 | (2006.01) |
| C12M 1/12 | (2006.01) |
| C12M 1/00 | (2006.01) |
| C12P 3/00 | (2006.01) |

(52) U.S. Cl.
CPC ............ *C12M 21/04* (2013.01); *C12M 21/16* (2013.01); *C12M 25/18* (2013.01); *C12M 29/02* (2013.01); *C12P 3/00* (2013.01); *Y02E 60/36* (2013.01)

(58) Field of Classification Search
CPC . C12M 21/04; C12M 21/16; C12M 25/14–18
See application file for complete search history.

(56) References Cited

U.S. PATENT DOCUMENTS

| 6,524,843 B1 | 2/2003 | Blais et al. |
| 6,620,614 B1 | 9/2003 | Lüth et al. |
| 2005/0059141 A1 | 3/2005 | Wismar |
| 2009/0305391 A1 | 12/2009 | Parent et al. |
| 2015/0099286 A1 | 4/2015 | Alitalo et al. |

FOREIGN PATENT DOCUMENTS

| RU | 2235767 C2 | 9/2004 |
| RU | 2359026 C2 | 6/2009 |
| WO | 2013167806 A1 | 11/2013 |

OTHER PUBLICATIONS

International Search Report, Application No. PCT/FI2015/050880, 4 pages, dated Mar. 4, 2016.

(Continued)

*Primary Examiner* — William H. Beisner
(74) *Attorney, Agent, or Firm* — FisherBroyles, LLP

(57) ABSTRACT

The present invention relates to a solid state fermentation process for producing hydrogen, and to a bioreactor and solid support for use in the fermentation process.

7 Claims, 1 Drawing Sheet

(56) References Cited

OTHER PUBLICATIONS

Klasson et al., "Methane Production from Synthesis Gas Using a Mixed Culture of R. rubrum, M. barkeri, and M. formicicum", Applied Biochemistry and Biotechnology, pp. 317-328, vol. 24/25 (1990).

Wolfrum et al., "Bioreactor Design Studies for a Novel Hydrogen-Producing Bacterium," Proceedings of the 2001 U.S. DOE Hydrogen Program Review, Baltimore, MD, US, pp. 11-22, Apr. 17, 2001.

Merida, et al., "Enhanced Hydrogen Production from Indirectly Heated, Gasified Biomass, and Removal of Carbon Gas Emissions Using a Novel Biological Gas Reformer", International Journal of Hydrogen Energy, pp. 283-290, vol. 29 (2004).

International Preliminary Report on Patentability, Application No. PCT/FI2015/050880, 11 pages, dated Dec. 12, 2016.

Finnish Search Report, Application No. 20146125, 2 pages, dated Jun. 30, 2015.

Search Report for PCT/FI2015/050880, filed Dec. 14, 2015, Registration No. 2017125510/10(044030), dated Apr. 6, 2018.

Official Action (translated) received in Application No. 2017125510/10(044030).

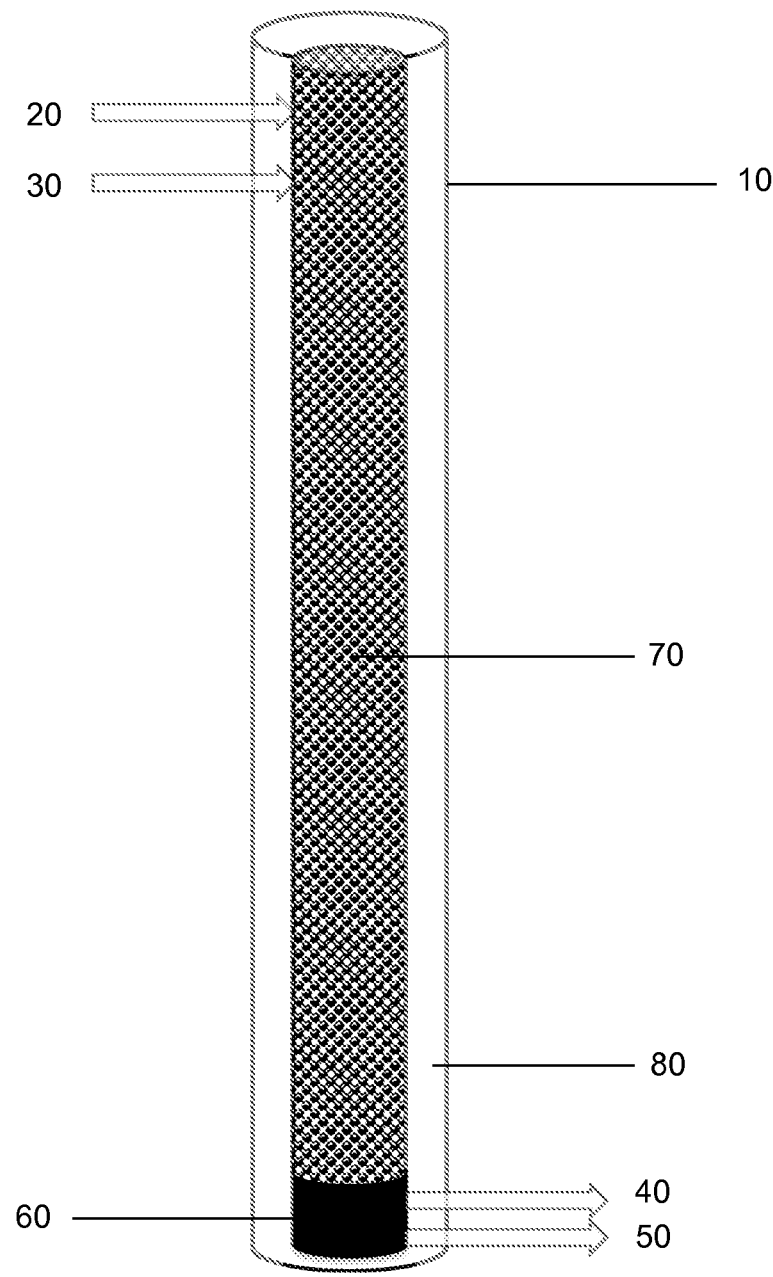

BIOREACTOR AND FERMENTATION PROCESS FOR PRODUCING HYDROGEN

CROSS-REFERENCE TO RELATED APPLICATIONS

This application is a National Stage application of International Application No. PCT/FI2015/050880, filed Dec. 14, 2015, which claims priority to Finnish Application No. 20146125, filed Dec. 19, 2014, which are incorporated by reference herein in their entireties.

BACKGROUND

Field

The present invention relates to a solid state fermentation process for producing hydrogen, and to a bioreactor and solid support for use in said process.

Related Art

Hydrogen ($H_2$) is the simplest and the most plentiful element in the universe. However, it is always combined with other elements and only small quantities occur naturally as gas on earth.

Hydrogen may be produced by converting carbon monoxide (CO) to carbon dioxide ($CO_2$) and hydrogen ($H_2$) through a reaction with water ($H_2O$) in a water-gas shift reaction: $CO + H_2O \rightarrow CO_2 + H_2$. The reaction may be catalyzed by two alternative ways: inorganically using metal catalysts at temperatures of some hundred degrees Celsius, or microbiologically at some tens of degrees Celsius.

Owing to the very high operating temperature required and the explosive nature of hydrogen, hydrogen production in inorganic catalysers is a challenging task. This drawback can be avoided by using microbiologically catalyzed hydrogen fermenting bioreactors.

General environmental factors affecting microbial activity in any bioreactor include water content, temperature, pH, partial pressure of dissolved oxygen and other gases, nutritional conditions, and degree of homogeneity. Traditionally, fermentation processes are carried out either in liquid or on moist solid particles. Mechanical agitation or stirring is the most common way of enhancing the transfer of gases and other substances in the bioreactor. Liquid fermentation coupled with agitation provides bioreactors that are easy to control. However, such bioreactors are expensive and agitation consumes high amounts of energy. If the bioreaction uses gaseous substrates and/or produces gaseous end products, securing efficient gas transfer at low cost becomes extremely difficult.

Solid-state fermentation processes provide several advantages over liquid fermentation processes. For instance, water which is a prerequisite for microbial growth exists mainly as adsorbed into or bound capillarily to the moist solid particles in the solid-state bioreactors. Thus, the water phase in the spaces between the particles is discontinuous and most of the inter-particle space is filled by the gas phase. This makes it relatively easy to feed gaseous starting materials into the bioreactor by applying pressure. In addition, any gaseous end products may exit the system by pressure differences. No agitation is needed in solid-state bioreactors and, thus, instrumentation may be far simpler than in liquid bioreactors. Furthermore, remarkably dense microbial growth on the moist solid particles may be achieved, resulting in high fermentation efficiency. The solid-state approach is particularly suitable for large-scale fermentation processes and bioreactors in cases where the unit prices of the end products are low and, thus, the aim is to build low-cost bioreactors with low maintenance costs.

Trickle bed reactors are a type of fixed bed bioreactors for use in solid-state fermentation. In these reactors, liquid trickles over a packed bed of catalyst particles by gravity while gas flows simultaneously either in a concurrent or countercurrent manner. Thus, trickle bed has so high saturation level with liquid that moist catalyst particles cannot cause suction for liquid. Sufficient liquid feed is particularly important in fermentation reactions which consume the liquid.

Wolfrum and Watt disclose in Proceedings of the 2001 U.S. DOE Hydrogen Program Review, Baltimore, Md., United States, Apr. 17-19, 2001, pp. 11-22 use of a countercurrent trickle bed reactor for metabolizing CO by naturally occurring microorganisms along with water to produce H2 and CO2. Water was provided in a sterile culture medium, fresh aliquots of which were periodically added to the reactor to replenish the liquid phase. Support materials tested included glass beads of two different diameters, cellulosic sponge material, and milled hardwood. The reactor performance differed from support material to support material.

There are some disadvantages associated with solid-state fermentation, too. For instance, owing to varying physical and chemical environmental conditions, the microbial growth and its efficacy may be unevenly distributed over the solid particles. Since the solid-state bioreactors cannot be homogenized by stirring, the availability of nutrients to the micro-organisms may be uneven and it may be difficult to provide pH control. Furthermore, aeration or transfer of gaseous substances between different parts of the bioreactor may be limited. This may, for instance, be due to a blockade of the inter-particle space by condensing water, or water produced in the bioreaction. On the other hand, in cases where the bioreaction does not produce water, the solid particles may desiccate owing to gravity or gas flows, thus lowering the fermentation capacity of the micro-organisms.

The present invention aims at avoiding disadvantages of conventional solid-state bioreactors, especially when the bioreaction involves gaseous starting materials and/or reaction products, and low building and maintenance costs are desired.

SUMMARY

One aspect of the present invention relates to a bioreactor comprising a CO feeding system, a $H_2O$ feeding system, an effluent recirculation system, and a $H_2$ and $CO_2$ collection system, wherein the bioreactor is loaded with a porous solid support at least 10% of which has a pore volume size which results in a water suction of about 0.01 to about 1.0 bar as compared to free water, wherein said water suction level for said at least 10% of the pore volumes is obtained by loading the bioreactor with a solid support which comprises either (i) particles having a diameter of 0.1 mm to 10 mm for at least 20% of the particles;

(ii) a spongy material having a pore size of 0.1 mm to 10 mm for at least 10% of its pores;

(iii) a filamentous material, wherein the diameter of inter-filamentous spaces is from 0.1 mm to 10 mm for at least 10% of its inter-filamentous spaces; or (iv) any mixture of (i) to (iii), and wherein the solid support is inoculated with micro-organisms catalysing water-gas shift reaction; and the bioreactor comprises a solid phase, a liquid phase and a gaseous phase, wherein the volume of the gaseous phase is 20% to 80% of the volume of the bioreactor.

Another aspect of the invention relates to process for generating hydrogen by solid state fermentation, comprising the steps of a) providing a bioreactor according to any embodiment of the present invention, b) feeding CO and $H_2O$ into the reactor, c) anaerobically bioconverting said CO and $H_2O$ into hydrogen and carbon dioxide, and d) collecting hydrogen from the bioreactor.

Still another aspect of the invention relates to the use of a solid support comprising (i) particles having a diameter of 0.1 mm to 10 mm for at least 20% of the particles; (ii) a spongy structure material having a pore size of 0.1 mm to 10 mm for at least 10% of its pores; or (iii) a filamentous structure material, wherein the diameter of inter-filamentous spaces is from 0.1 mm to 10 mm for at least 10% of its inter-filamentous spaces; or a mixture thereof, for generating hydrogen from carbon monoxide and water in a solid state fermentation process.

Specific embodiments of the invention are set forth in the dependent claims. Other aspects, details, embodiments and advantages of the present invention will become apparent from the following drawings, detailed description and examples.

BRIEF DESCRIPTION OF THE DRAWING

In the following the invention will be described in greater detail by means of preferred embodiments with reference to the attached drawing, in which FIG. 1 shows a schematic representation of an exemplary hydrogen bioreactor.

DETAILED DESCRIPTION

The present invention relates to an unsaturated solid state fermentation (SSF) process and a bioreactor, wherein carbon monoxide (CO) and water ($H_2O$) are converted into hydrogen ($H_2$) and carbon dioxide ($CO_2$) by micro-organisms which are grown on a porous solid support in the bioreactor and which are capable of catalysing a water-gas shift (WGS) reaction.

Micro-organisms suitable for use in the present SSF process and bioreactor may be obtained from various sources such as culture collections or be isolated, for instance, from swamps, such as peat bogs or sphagnum bogs, or other wetlands, or from digestive organs or a digestive tract. The choice of the micro-organism in the present process may depend on various factors including, but not limited to, nutrient, temperature, and pH requirements of a given micro-organism as readily understood by a skilled person. In some embodiments, micro-organisms which work well in lower temperatures may be preferred because less energy would be needed for heating the bioreaction. A person skilled in the art is able to determine whether or not a micro-organism is suitable for being used in different embodiments of the present invention.

The bioreactor according to the present invention comprises three major phases, i.e. a solid phase comprising a porous solid support, a liquid phase comprising water employed in the fermentation process, and a gaseous phase comprising CO, $H_2$, and $CO_2$. The volume of the gaseous phase should be 20% to 80% of the volume of the bioreactor in order to achieve a large enough liquid-solid interface.

Furthermore, the greater the gaseous phase, the longer the reaction time and, thus, the more efficient the bioreactor. It is important that the solid phase is distributed evenly in the dispersing gaseous phase throughout the bioreactor.

Importantly, the present bioreactor is unsaturated with the liquid phase. As used herein, the term "unsaturated" refers to not being saturated, i.e. having the suction to contain still more of the liquid phase, typically water. Consequently, the present bioreactor is fundamentally different from saturated bioreactors, such as trickle bed reactors. As used herein the term "saturated" refers to being saturated, i.e. not having the suction to bind any more of liquid, such as water.

Capillary conductivity and sufficient inter-solid-support gas volume define the gas and liquid flow characteristics through the solid support. Adequate capillary conductivity is required to ensure that the gas and liquid transfer can be distributed evenly and maintained at the desired levels for the duration of the fermentation process. Furthermore, humidity in the bioreactor must be high enough to enable the micro-organisms to grow on the solid support. On the other hand, too high moisture content would be harmful to at least some types of micro-organisms, as well as block the gas transfer by filling the inter-solid-support space.

Solid support suitable for use in the present invention must be porous in order to obtain sufficient fermentation conditions as described herein. Water binds to the pores of the solid support by capillary forces resulting from adsorption and surface tension. Intensity of the binding may be expressed by pressure units, such as bars. A given pore size corresponds to a certain binding intensity. Assuming that the pores are cylindrical tubes, the radius of the largest pores filled with water may be calculated from the following equation:

$$r = 2\gamma/h\rho g,$$

wherein r is the radius of the pore (m);
γ is the surface tension of water, i.e. 0.073 N/m;
h is the water suction expressed as the height of the water column (m) (the absolute value of capillary potential of water);
ρ is the density of water, i.e. 1000 kg/m³;
g is gravitational acceleration, i.e. 9.81 m/s².

This equation is often presented in a simplified form:

$$D = 0.3/h,$$

wherein D is the diameter of the pore (cm); and
h is the water suction expressed as the height of the water column (cm) (the absolute value of capillary potential of water).

Solid support suitable for use in the present invention should be such that at least 10% of the pore volumes have pore diameters resulting in a water suction of about 0.01 to about 1.0 bar as compared to free water. This water suction level is a prerequisite for the present bioreactor being functional in unsaturated conditions.

Said required water suction level of about 0.01 to about 1.0 bar for at least 10% of the pore volumes is achieved by using solid support according to any embodiment set forth below.

In some embodiments, the solid support may comprise or be in the form of particles having a diameter of 0.1 mm to 10 mm. Any one particle size within this range or any combination thereof may be used in the present process and the bioreactor. Non-limiting examples of suitable average diameters of the pores lie within the range of about 10 nm to about 100 nm, and suitable particle materials include, but are not limited to, material mixtures comprising vermiculite, modified vermiculites, vermiculite-like materials, or synthetic vermiculites; synthetic cation-exchange resins; various peat types; other organic materials; and mixtures thereof as long as they have or they provide the required physical and chemical characteristics described herein. It is particularly important that the solid support provides a gaseous phase, the volume of which is 20% to 80% of the volume of the bioreactor, and which is distributed evenly throughout the bioreactor.

In some other embodiments the solid support may comprise or be in the form of a spongy structure having a pore size distribution within the range of about 0.1 mm to about 10 mm for at least 10% of its pore volumes. Non-limiting examples of suitable spongy materials include synthetic spongy materials, such as foamed plastic polymers, as well as natural sponges.

In some yet other embodiments, the solid support may be provided as a filamentous structure. In such cases, inter-filamentous spaces may be regarded as the pores of the filamentous solid support, and their diameter distribution should lie within the range of about 0.1 mm to about 10 mm for at least 10% of the inter-filamentous spaces.

A non-limiting example of a suitable filamentous material includes steel wool. As steel wool does not have any cation-exchange properties it may be provided in a mixture with particles having sufficient cation-exchange properties. Alternatively or in addition, steel wool may be coated or applied with an organic material, such as polyacrylamide, in order to achieve sufficient cation-exchange properties.

The porous solid support may also be any admixture of particles, spongy materials and filaments as long as it fulfils the physical requirements set forth herein.

The porosity of the solid support not only affects the moisture conditions in the bioreactor but also provides a large attachment surface for micro-organisms and protects them from flushing. In addition, porosity increases the specific surface area of the solid support. In some embodiments, the specific surface area of the solid support is at least 5 m$^2$/g.

High specific surface area, in turn, results in high ion-exchange capacity of the porous solid support. In order to be suitable for use in the present fermentation process, the solid support should have high cationic exchange capacity, typically higher than 0.1 mmol/g. Since most nutrient substances are cationic, cation-exchange properties of the solid support are more important than anion-exchange properties. However, in some embodiments, the solid support may also possess anion-exchange properties. In some further embodiments, the cation-exchange capacity and the anion-exchange capacity may even be almost equal to each other.

Furthermore, high specific surface area together with high cation-exchange capacity results in formation of a biofilm. This, in turn, increases the efficiency of the fermentation process due to high micro-organism content.

The above-mentioned properties of the solid support provide sufficient buffering properties in the fermentation process. When the solid support, owing to its cation-exchange capacity, is capable of exchanging hydrogen and/or hydroxyl ions with a liquid phase, there should be no need for additional pH controlling.

Solid supports not suitable for use in the present invention include materials that are inactive in terms of their cation exchange capacity. More specific examples of such materials include silica-based materials such as glass, wood-based materials, most plastics (unless they are couples with active groups), and most stone materials, such as feldspar and quartz. It is noteworthy that although vermiculite exists in forms having a sufficient cation exchange capacity, it is not a suitable solid support material to be used alone in the present bioreactor. This is because it is not possible to achieve a sufficient gaseous phase volume with sole vermiculite. Spontaneous compaction through wetting and drying effect would reduce the gaseous phase volume below 20% of the volume of the bioreactor even if in some specific cases it might be possible to achieve an initial gaseous phase volume of slightly over 20% of the volume of the bioreactor. Thus, if vermiculite is to be employed in the present bioreactor, it needs to be provided in a mixture with other, non-flat materials, such as perlite, in order to fulfil the requirement that the volume of the gaseous phase must be 20% to 80% of the volume of the bioreactor.

The present process may be carried out in a bioreactor which is, for instance, a glass, stainless steel, or plastic tank or vessel. The material of the bioreactor should be non-toxic to the micro-organisms used in the process. The size and shape of the bioreactor may vary within a range known to a person skilled in the art depending on different parameters, such as the choice of the solid support material. Preferably, the size is suitable for industrial scale hydrogen production. The bioreactor should be low-cost, easy to operate, and reliable.

An exemplary bioreactor is illustrated in FIG. 1. The upper end of the bioreactor vessel 10 is provided with a CO distribution system 20 and a water distribution system 30 whereas the lower end of the vessel 10 is provided with $H_2$ and $CO_2$ collection system 40 and a effluent collection system 50. The bottom part of the bioreactor vessel is covered with a layer of crushed limestone 60, while the remainder of the vessel is loaded with a porous solid support material 70 described herein. The bioreactor vessel is surrounded by a heating water circulation 80.

In some embodiments, the effluent collection system 50 is an effluent recirculation system which is connected to the water distribution system 30. As used herein, the term "effluent" refers to an outflowing of water from the bioreactor.

Produced $H_2$ and $CO_2$ can be separated from each other by standard methods known in the art. This separation step may or may not be included in the present fermentation process.

The bioreactor may be provided with various sensors for monitoring desired parameters such as the temperature, pH, and humidity in the reactor. Such sensors are readily available in the art. The bioreactor may also be provided with a gas analyser for monitoring the operation of the bioreactor and the yield of hydrogen production.

Temperature control of the present process may be obtained e.g. by connecting a closed water circulation system to the bioreactor. Such a system may provide either heating or cooling of the process depending on the needs of a given micro-organism. Heat is transferred between the water circulation system and the bioreactor by conductivity. Other means and methods for adjusting the temperature of the present process are well known in the art.

Carbon monoxide used as a starting material in the present fermentation process may be captured from any suitable source including, but not limited to syngas from fossil fuels such as coal, oil or gas in power plants.

Micro-organisms require additional nutrients such as nitrogen, nickel, and/or cobalt for their growth. These substances may be supplied during the fermentation process or, preferably, provided attached to a solid support having cation-exchange capacity as described above thus resulting in a self-sustained process in this respect. Nitrogen may be given e.g. in the form of urea or ammonium carbonate. In some embodiments, wood ash may be used to provide additional nutrients to the micro-organisms. The specific concentration on these elements depends on the micro-organism being used.

A functional bioreactor and hydrogen fermentation process according to the present embodiments may be set up in a short period of time, such as a couple of days. After the fermentation process is up and running, the bioreactor will continue to produce hydrogen and carbon dioxide for a period of several months or years. In some embodiments, the efficiency of the bioreaction may exceed several watts per litre and/or the purity of gas produced may be near theoretical values 50% hydrogen and 50% carbon dioxide. The more efficient the bioreactor by volume, the smaller its size may be.

Hydrogen collected from the bioreactor may be used for any desired purpose including, but not limited to, fuel cells. Hydrogen may also be used as a starting material for producing various hydrocarbons such as methane.

It will be obvious to a person skilled in the art that, as technology advances, the inventive concept can be implemented in various ways. The invention and its embodiments are not limited to the examples described below but may vary within the scope of the claims.

Example 1

A 18.15 litre vertical bioreactor illustrated in FIG. 1 was constructed from a polyvinyl chloride sewer pipe having a diameter of 160 mm and height of 1000 mm. Two nylon inlet tubes for CO and bioreactor effluent delivery were fitted to the upper part of the pipe. The lower part of the pipe was provided with two outlet tubes, one for gas collection and the other for possible maintenance procedures such as recycling the bioreactor effluent. The lower part of the sewer pipe was covered with a 10 cm thick layer of crushed limestone and the rest of the bioreactor was filled with a solid support, vermiculite. Prior to the filling 2.5 kg of vermiculite was mixed with 700 g of perlite, 40.0 g of wood ash, 0.8 g of hydrated cobalt sulphate ($CoSo4.7H_2O$), and 0.8 g of hydrated nickel chloride ($NiCl_2.6H_2O$). The bioreactor was inoculated with a 8.4 litre aqueous slurry of micro-organisms obtained from an earlier bioreactor and stored in a CO by pumping through the inlet of the upper part of the bioreactor.

A water circulation system was used for heating the bioreactor. The temperature of the heating water was adjusted to a desired level, typically 53 to 55° C.

Bioreactor effluent and CO were conveyed to the bioreactor through two nylon inlet tubes fitted to the upper part of the bioreactor. The proportion and mode of the CO and bioreactor effluent delivery were adjusted at the beginning of the fermentation process on the basis of variables such as dryness of the bioreactor.

Gas samples were collected from the reactor output. CO, $CO_2$ and $CH_4$ were analysed with a Hewlett Packard 6890 gas chromatograph by using TCD detector. $H_2S$, $H_2$ and $O_2$ were measured with a COMBIMASS GA-m gas analyser by using electrochemical sensors. Because of the high concentration of the measured gas components the sample gas was diluted before measuring the gas composition. For CO, $CO_2$ and $CH_4$ measurement dilution was 100 fold. For $H_2$, $H_2S$ and $O_2$ measurement dilution was 500 to 1000 fold. Continuous measurement of the output gas $CO_2$ level was done with a Dräger GasVisi X-am 7000 gas analyser.

When the rate of CO feeding varied between 30 litre/day and 300 l/day, the average efficiency of the bioreactor varied between 0.2 watt/litre and 2 watt/litre, while the $H_2$ and $CO_2$ were 45 Vol % and 45 Vol % respectively.

What is claimed is:

1. An unsaturated bioreactor comprising a CO feeding system, a $H_2O$ feeding system, an effluent recirculation system, and a $H_2$ collection system,
   wherein the bioreactor is loaded with a porous solid support, at least 10% of which has a pore volume size which results in a water suction of about 0.01 to about 1.0 bar as compared to free water,
   wherein said water suction level for said at least 10% of the pore volumes is obtained by loading the bioreactor with a solid support which comprises:
   (i) particles having a diameter of 0.1 mm to 10 mm for at least 20% of the particles; or
   (ii) a spongy material having a pore size of 0.1 mm to 10 mm for at least 10% of its pores; or
   (iii) a filamentous material, wherein the diameter of inter-filamentous spaces is from 0.1 mm to 10 mm for at least 10% of its inter-filamentous spaces; or
   (iv) any mixture of (i) to (iii), and
   wherein the solid support is inoculated with micro-organisms catalysing water-gas shift reaction; and
   the bioreactor comprises a solid phase, a liquid phase and a gaseous phase, wherein the volume of the gaseous phase is 20% to 80% of the volume of the bioreactor, wherein the bioreactor is not a trickle bed reactor.

2. The bioreactor according to claim 1, wherein said solid support has a cationic exchange capacity of at least 0.1 mmol/g.

3. The bioreactor according to claim 1, wherein said solid support has a specific surface area of at least 5 $m^2/g$.

4. The bioreactor according to claim 1, wherein said solid support particles are selected from the group consisting of material mixtures comprising vermiculite, material mixtures comprising modified vermiculite, material mixtures comprising vermiculite-like material, material mixtures comprising synthetic vermiculites, synthetic cation exchange resins, various peat types, and mixtures thereof.

5. The bioreactor according to claim 1, wherein said spongy material is selected from the group consisting of synthetic spongy materials and natural sponges.

6. The bioreactor according to claim 1, wherein said filamentous material is coated or non-coated steel wool.

7. An unsaturated process for generating hydrogen by solid state fermentation, comprising:
   a) providing an unsaturated bioreactor comprising a CO feeding system, a $H_2O$ feeding system, an effluent recirculation system, and a $H_2$ collection system, wherein the bioreactor is loaded with a porous solid support, at least 10% of which has a pore volume size which results in a water suction of about 0.01 to about 1.0 bar as compared to free water,
   wherein said water suction level for said at least 10% of the pore volumes is obtained by loading the bioreactor with a solid support which comprises:
   (i) particles having a diameter of 0.1 mm to 10 mm for at least 20% of the particles; or
   (ii) a spongy material having a pore size of 0.1 mm to 10 mm for at least 10% of its pores; or
   (iii) a filamentous material, wherein the diameter of inter-filamentous spaces is from 0.1 mm to 10 mm for at least 10% of its inter-filamentous spaces; or
   (iv) any mixture of (i) to (iii), and
   wherein the solid support is inoculated with micro-organisms catalysing water-gas shift reaction; and the bioreactor comprises a solid phase, a liquid phase and a gaseous phase, wherein the volume of the gaseous phase is 20% to 80% of the volume of the bioreactor, wherein the bioreactor is not a trickle bed reactor, b) feeding CO and $H_2O$ into the reactor;

c) anaerobically bioconverting said CO and $H_2O$ into hydrogen and carbon dioxide; and d) collecting said hydrogen and carbon dioxide from the bioreactor.

\* \* \* \* \*